(12) United States Patent
Couturier et al.

(10) Patent No.: US 7,199,214 B2
(45) Date of Patent: Apr. 3, 2007

(54) PROCESS FOR THE PREPARATION OF POLYALKOXYAMINES WHICH CAN BE USED AS INITIATORS FOR THE RADICAL POLYMERIZATION OF POLYFUNCTIONAL LIVING (CO)POLYMERS

(75) Inventors: Jean-Luc Couturier, Lyons (FR); Olivier Guerret, Mazerolles (FR); Stéphanie Magnet, Morlanne (FR)

(73) Assignee: Arkema France, Puteaux (FR)

( * ) Notice: Subject to any disclaimer, the term of this patent is extended or adjusted under 35 U.S.C. 154(b) by 0 days.

(21) Appl. No.: 10/969,711

(22) Filed: Oct. 20, 2004

(65) Prior Publication Data
US 2005/0107577 A1 May 19, 2005

Related U.S. Application Data

(60) Provisional application No. 60/514,287, filed on Oct. 24, 2003.

(30) Foreign Application Priority Data
Oct. 24, 2003 (FR) .................................. 03 12452

(51) Int. Cl.
*C08G 73/00* (2006.01)
(52) U.S. Cl. ...................... 528/422; 528/425; 528/398; 525/333.8; 514/114; 558/190
(58) Field of Classification Search ............... 528/422, 528/425, 398; 525/333.8; 514/114; 558/190
See application file for complete search history.

(56) References Cited

U.S. PATENT DOCUMENTS 6,569,967 B1 5/2003 Couturier et al.
6,646,079 B2 11/2003 Guerret et al.
6,657,043 B1 12/2003 Guerret et al.
6,659,967 B1 12/2003 Steinberg

OTHER PUBLICATIONS

Couturier et al, Alkoxyamines derived from phosphorus containing nitroxides and their use, Elf Atochem S.A., France, 2000, Chem Abstract 133: 177640.*
"Design and Use of .beta.-Phosphorous Nitroxides and Alkoxyamines in Controlled/"Living"Free Radiacal Polymerizations", LeMereier, et al., Macromolecular Symp., vol. 182, 2002, pp. 225-247.

* cited by examiner

*Primary Examiner*—Duc Truong
(74) *Attorney, Agent, or Firm*—Steven D. Boyd

(57) ABSTRACT

The present invention is directed to a process for the preparation of polyalkoxyaminies from monoalkoxyamine (s) of formula (I)

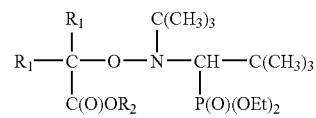

and of at least one polyunsaturated compound of formula (II):

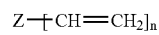

and the preparation of polyfunctional living (co)polymers by polymerization by the radical route of one or more vinyl monomers in the presence of the polyalkoxyamines thus prepared.

24 Claims, 1 Drawing Sheet

PROCESS FOR THE PREPARATION OF POLYALKOXYAMINES WHICH CAN BE USED AS INITIATORS FOR THE RADICAL POLYMERIZATION OF POLYFUNCTIONAL LIVING (CO)POLYMERS

This application claims the benefit of Provisional Application Ser. No. 60/514,287, filed Oct. 24, 2003.

FIELD OF THE INVENTION

A subject-matter of the present invention is polyalkoxyamines obtained from monoalkoxyamines and from polyfunctional compounds which can be used in particular as radical polymerization initiators for the synthesis of polyfunctional living copolymers.

BACKGROUND

Recent developments in controlled radical polymerization have demonstrated the advantage of polyalkoxyamines, as described in Accounts of Chemical Research, 1997, 30, pages 373–382.

These polyalkoxyamines, under the effect of heat, in the presence of an olefin which can be polymerized by the radical route, initiate the polymerization while making it possible to control it.

The mechanism of this control can be represented diagrammatically as follows:

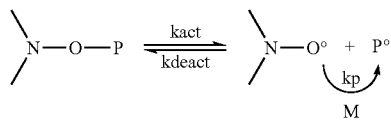

with M representing a polymerizable olefin and P the growing polymer chain.

The key to the control is related to the constants $k_{deact}$, $k_{act}$ and $k_p$ (T. Fukuda and A. Goto, Macromolecules 1999, 32, pages 618 to 623). If the ratio $k_{deact}/k_{act}$ is too high, the polymerization is blocked, whereas, when the ratio $k_p/k_{deact}$ is too high or when the ratio $k_{deact}/k_{act}$ is too low, the polymerization is not controlled.

P. Tordo et al., Polym. Prep. 1997, 38, pages 729 and 730, and C. J. Hawker et al., Polym. Mater. Sci. Eng., 1999, 80, pages 90 and 91, have found that β-substituted alkoxyamines make it possible to efficiently initiate and control the polymerization of several types of monomers, whereas the alkoxyamines derived from TEMPO [such as (2',2',6',6-tetramethyl-1'-piperidnyloxy)methylbenzene, mentioned in Macromolecules, 1996, 29, pages 5245–5254] control, under conditions which can be operated industrially, only the polymerizations of styrene derivatives.

In U.S. Pat. No. 6,657,043, the polyalkoxyamines make it possible to synthesize polymers and copolymers with well-defined architectures. For n=2 (dialkoxyamine), it is possible to synthesize triblock copolymers, each block resulting from monomers as different as alkyl acrylates and/or styrene derivatives, with excellent control of the polymerization and of the polydispersity and with very short polymerization reaction times.

Thus, for example, it is possible to successively polymerize two monomers M1 and M2:

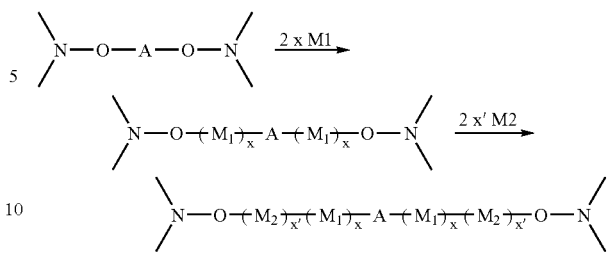

By way of example, M1=alkyl acrylate and M2=styrene.

Starting from trialkoxyamine (n=3), "star" polymers will be obtained.

The polyalkoxyamines can be synthesized by different methods. One method involves the reaction of a halogenated derivative $A(X)_n$ in the presence of an organometallic system, such as CuX/ligand (X=Cl or Br), according to a reaction of ATRA (Atom Transfer Radical Addition) type as described by D. Greszta et al. in Macromolecules, 1996, 29, 7661–7670. A process of this type is disclosed in U.S. Pat. No. 6,657,043 on behalf of the Applicant Company. Another method involves the reaction of a functional alkoxyamine, for example carrying an alcohol functional group, with a polyacid or a poly(acid chloride), as described, for example, by C. J. Hawker in Accounts of Chemical Research 1997, 30, 373–382. These methods exhibit the disadvantage of using reactants which have to be synthesized in one or more stages (polyhalogenated compounds, functional alkoxyamines) and of requiring relatively complex purification stages. Furthermore, the intermediates in these syntheses may be novel products which require developments and adaptations and/or modifications, indeed even complete replacement, of the industrial equipment, which is not favourable to the use of such syntheses on the industrial scale.

C. J. Hawker has also described, in Accounts of Chemical Research 1997, 30, 373–382, the preparation of a polyalkoxyamine by oligomerization of a functional alkoxyamine carrying a styrene double bond. However, the fact that the thermal stabilities of the polyalkoxyamine and of the starting alkoxyamine are equivalent makes it very difficult to control the synthesis of the polyalkoxyamine due to the concomitant formation of gels. Thus, the preparation of polyfunctional living polymers has also been envisaged by addition of a monofunctional living polymer to polyfunctional vinylbenzenes (see, for example, P. Chaumont in Macromolecules (2001), 34(12), 4109–4113) but, on proceeding in this way, the author has characterized products which are gelled as a result of the crosslinking.

DETAILED DESCRIPTION

Figure 1:
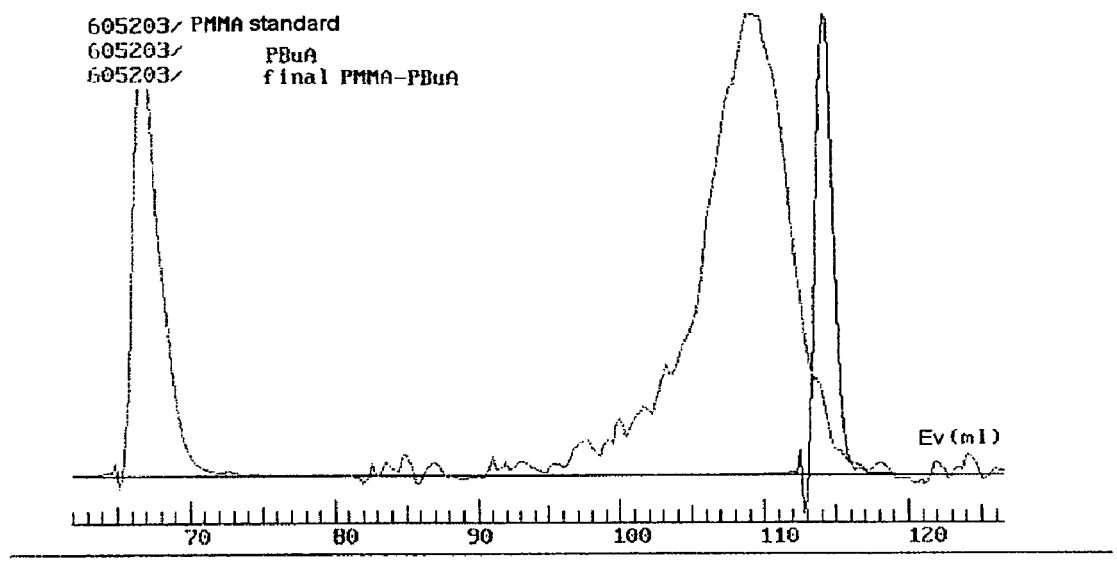
FIG. 1 is a characterization by Liquid Adsorption Chromatography of a PMMA standard, PBuA polymer and PMMA/PBuA/PMMA copolymer.

The inventors have discovered a novel process for the preparation of polyalkoxyamines which makes use of readily available reactants, which does not require a purification stage and which can be carried out in situ before the use in polymerization of these polyalkoxyamines (see below).

This process consists in reacting one or more alkoxyamines of formula (I)

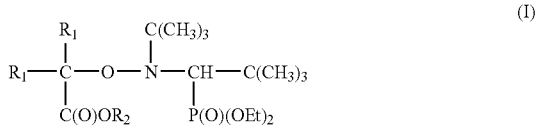

in which $R_1$ represents a linear or branched alkyl radical having a number of carbon atoms ranging from 1 to 3 and $R_2$ represents a hydrogen atom, a linear or branched alkyl radical having a number of carbon atoms ranging from 1 to 8, a phenyl radical, an alkali metal, such as Li, Na or K, or an ammonium ion, such as $NH_4^+$, $NBu_4^+$ or $NHBu_3^+$; preferably, $R_1$ is $CH_3$ and $R_2$ is H;

with at least one polyunsaturated compound of formula (II):

in which Z is an aryl group or can be represented by the formula $Z_1$-[X—C(O)]$_n$ where $Z_1$ represents a polyfunctional structure originating, for example, from a compound of polyol type, X is an oxygen atom, a nitrogen atom carrying a carbonaceous group or carrying a hydrogen atom, or a sulphur atom, and n is an integer greater than or equal to 2, in the presence or absence of solvent(s) preferably chosen from alcohols, such as ethanol, aromatic solvents, chlorinated solvents, ethers or polar aprotic solvents, at a temperature generally of between 0 and 90° C., preferably of between 25 and 80° C., the molar ratio of monoalkoxyamine(s) of formula (I) to polyunsaturated compound(s) of formula (II) being between 1.5 and 1.5 n, preferably between n and 1.25 n, this stage optionally being followed by a stage of evaporation of the optional solvent or solvents.

The polyunsaturated compound can be chosen from polyfunctional vinylbenzenes (Z=aryl group) or from polyfunctional acrylic derivatives (Z=$Z_1$-[X—C(O)]$_n$). Preferably, the unsaturated compound is divinylbenzene, trivinylbenzene, ethylene glycol diacrylate, 1,3-butanediol diacrylate, 1,4-butanediol diacrylate, 1,6-hexanediol diacrylate, neopentyl glycol diacrylate, cyclohexanedimethanol diacrylate, diethylene glycol diacrylate, triethylene glycol diacrylate, tetraethylene glycol diacrylate, dipropylene glycol diacrylate, tripropylene glycol diacrylate, polyethylene glycol diacrylates (sold by Sartomer under the names SR259, SR344 or SR610), hexanediol alkoxylate diacrylates (sold by Sartomer under the names CD561, CD564 or CD560), bisphenol A diacrylate, bisphenol A ethoxylate diacrylates (sold by Sartomer under the names SR349, SR601, SR602 or CD9038), trimethylolpropane triacrylate, pentaerythritol triacrylate, tris(2-hydroxyethyl)isocyanurate triacrylate, trimethylolpropane ethoxylate triacrylates (sold by Sartomer under the names SR454, SR499, SR502, SR9035 or SR415), glyceryl propoxylate triacrylate (sold by Sartomer under the name SR9020), trimethylolpropane propoxylate triacrylates (sold by Sartomer under the names SR492 and CD501), pentaerythritol tetraacrylate, ditrimethylolpropane tetraacrylate, pentaerythritol ethoxylate tetraacrylate (sold by Sartomer under the name SR494), dipentaerythritol pentaacrylate, caprolactone modified dipentaerythritol hexaacrylates (sold by Sartomer under the names Kayarad DCPA-20 and DCPA60) or dipentaerythritol pentaacrylate (sold by UCB Chemicals under the name DPHPA).

The specificity of the process for the preparation of the polyalkoxyamines lies in the fact that the alkoxyamines of formula (I) can produce, from a mean temperature, radicals:

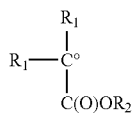

which can add to the polyunsaturated compound $Z-(CH=CH_2)_n$ to give novel radicals which will recombine with the nitroxide simultaneously generated in the reaction medium:

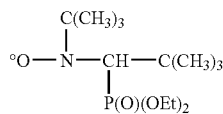

to give polyalkoxyamines carrying functional groups:

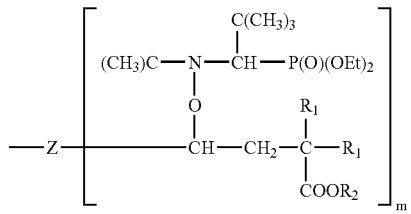

in which m is an integer greater than or equal to 2 and inferior or equal to n, which exhibit the advantage of being stable up to 80° C.

The differences in thermal stability between alkoxyamines (I) and the polyalkoxyamines formed makes it possible to avoid the formation of gels which may be brought about by the polymerization of (II).

The compounds are obtained as they are, i.e. by evaporation, for example under reduced pressure, and are identified by mass spectrometry and by $^1H$, $^{13}C$ and $^{31}P$ NMR spectrometry.

Another subject-matter of the present invention is a process for the preparation of polyfunctional living (co)polymers by polymerization of one or more vinyl monomers in the presence of the polyalkoxyamines prepared beforehand according to the process described above. This polymerization process makes it possible to access (co)polymers with controlled macromolecular architectures (block (co)polymers with a linear, star or hyperbranched structure or the like) starting from a single family of monoalkoxyamines.

Such a process can also be applied to preparing the mixture of alkoxyamines resulting in multimodal living polymers as disclosed in U.S. Pat. No. 6,646,079 on behalf of the Applicant Company.

In U.S. Pat. No. 6,657,043, the Applicant Company has shown that the polyalkoxyamines make it possible to synthesize polymers and copolymers with well-defined architectures. For n=2 (dialkoxyamine), it is possible to synthesize triblock copolymers, each block resulting from monomers as different as alkyl acrylates and/or styrene derivatives, with excellent control of the polymerization and of the polydispersity and with very short polymerization reaction times.

Thus, for example, it is possible to successively polymerize two monomers (or two mixtures of monomers) M1 and M2:

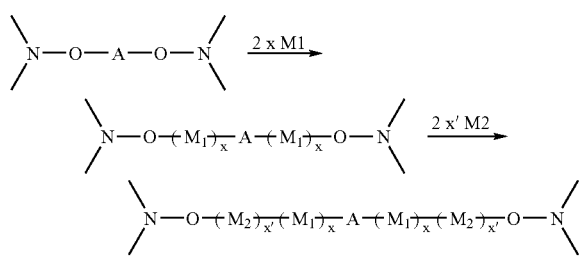

By way of example, M1=alkyl acrylate and M2=styrene.

Starting from a trialkoxyamine (n=3), "star" polymers will be obtained.

In the (co)polymerization process of U.S. Pat. No. 6,657,043, (co)polymers with controlled macromolecular architectures are prepared by radical polymerization starting from polyalkoxyamines in the presence of an excessive nitroxide, whereas, in the (co)polymerization process which is a subject-matter of the present invention, the polyalkoxyamines resulting from a single compound (I) which are obtained at a temperature generally of less than 90° C. can, for temperatures generally of greater than 90° C., give rise to a variety of macromolecular structures. Furthermore, the polymerization stages are controlled without introducing additional nitroxide.

The polyalkoxyamines can be used alone or in the presence of other radical initiators, such as organic or inorganic peroxides, azo derivatives and/or monofunctional alkoxyamines, to result in products exhibiting multimodal molecular weight distributions.

The polyalkoxyamines can be prepared prior to or simultaneously with the (co)polymerization.

The (co)polymerization can be carried out under the usual conditions known to a person skilled in the art, taking into account the monomer or monomers under consideration, in bulk, in solution (aqueous or organic), in emulsion, in miniemulsion or in suspension. The polymerization temperature is generally greater than 90° C.

The term "vinyl monomers" is understood to mean vinylaromatic monomers, such as styrene or substituted styrenes, dienes, such as butadiene or isoprene, acrylic monomers, such as acrylic acid, alkyl or aryl acrylates or functional acrylates which are optionally halogenated or carriers of siloxane functional groups, methacrylic monomers, such as methacrylic acid, alkyl or aryl methacrylates or functional methacrylates which are optionally halogenated or carriers of siloxane functional groups, such as methyl methacrylate, acrylonitrile, acrylamide or substituted acrylamides, such as N,N-dimethylacrylamide, 4-acryloylmorpholine, methacrylamide or substituted methacrylamides, vinylpyridine, vinylpyrrolidinone, vinyl chloride, vinylidene difluoride or a mixture of at least two abovementioned monomers.

The polymers obtained are polyfunctional living (co)polymers carrying alkoxyamine functional groups. They can be themselves recharged one or more times in a radical polymerization process with the abovementioned vinyl monomers to result in block copolymers with a linear, star or hyperbranched structure which can be characterized by GPC (Gel Permeation Chromatography), LAC (Liquid Adsorption Chromatography) and DMA (Dynamic Mechanical Analysis).

The examples which follow illustrate the invention.

EXAMPLE 1

Preparation of a Polyalkoxyamine from Monoalkoxyamine with $R_1$=$CH_3$ and $R_2$=H and from 1,4-Butanediol Diacrylate A. Synthesis of the Monoalkoxyamine of Formula (I) Where $R_1$=$CH_3$ and $R_2$=H (2-methyl-2-[N-(tert-butyl)-N-(1-diethoxyphosphoryl-2,2-dimethylproyyl)aminoxyl]-propionic acid)

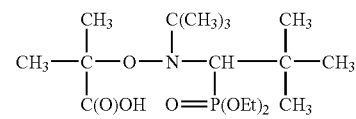

500 ml of degassed toluene, 35.9 g of CuBr (250 mmol), 15.9 g of copper power (250 mmol) and 86.7 g of N,N,N',N',N''-pentamethyldiethylenetriamine (PMDETA) (500 mmol) are introduced into a 2 l glass reactor purged with nitrogen and then a mixture comprising 500 ml of degassed toluene, 42.1 g of 2-bromo-2-methylpropionic acid (250 mmol) and 78.9 g of nitroxide of the formula

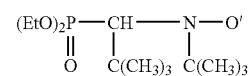

named SG1 at 84%, i.e. 225 mmol, is introduced with stirring at ambient temperature (20° C.).

The reaction medium is left to react at ambient temperature for 90 min with stirring and is then filtered. The toluene filtrate is washed twice with 1.5 l of a saturated aqueous $NH_4Cl$ solution.

A yellowish solid is obtained which is washed with pentane to give 51 g of 2-methyl-2-[N-(tert-butyl)-N-(1-diethoxyphosphoryl-2,2-dimethylpropyl )aminoxy]propionic acid (60% yield).

Analytical results are given below:

molar mass determined by mass spectrometry: 381.44 g.mol$^{-1}$ (for $C_{17}H_{36}NO_6P$)

elemental analysis (empirical formula: $C_{17}H_{36}NO_6P$): % calculated: C=53.53; H=9.51; N=3.67. % found: C=53.57; H=9.28; N=3.77.

melting carried out on a Büchi B-540 device: 124° C./125° C.

$^{31}$P NMR (CDCl$_3$): δ 27.7
$^1$H NMR (CDCl$_3$):
  δ 1.15 (singlet, 9H on carbons 15, 21 and 22),
  δ 1.24 (singlet, 9H on carbons 17, 23 and 24),
  δ 1.33–1.36 (multiplet, 6H on carbons 4 and 7),
  δ 1.61 (multiplet, 3H on carbon 18),
  δ 1.78 (multiplet, 3H on carbon 13),
  δ 3.41 (doublet, 1H on carbon 9),
  δ 3.98–4.98 (multiplet, 4H on carbons 3 and 6)
  δ (singlet, —OH).
$^{13}$C NMR (CDCl$_3$):

| Carbon atom number | δ |
|---|---|
| 3 and 6 | 60.28–63.32 |
| 9 | 69.86 |
| 12 | 63 |
| 13 | 28.51 |
| 14 | 36.04 |
| 15, 21 and 22 | 29.75 |
| 16 | 63.31 |
| 17, 23 and 24 | 28.74 |
| 18 | 24.08 |
| 19 | 176.70 | kd (120° C.)=0.2 s$^{-1}$

B. Preparation of the Polyalkoxyamine

The following are introduced into a 100 ml round-bottom flask purged with nitrogen:
  2 g of alkoxyamine prepared in A (2.1 equivalents)
  0.55 g of 1,4-butanediol diacrylate, sold by Aldrich, with a purity of 90% (1 equivalent)
  5.7 ml of ethanol The mixture is heated at reflux (temperature 78° C.) for 20 h and then the ethanol is evaporated under vacuum. 2.5 g of a highly viscous yellow oil are obtained.

$^{31}$P NMR analysis shows the complete disappearance of the methacrylic acid-SG1 alkoxyamine (27.4 ppm) and the appearance of the dialkoxyamine (multiplet at 24.7–25.1 ppm).

Analysis by electrospray-type mass spectrometry shows the mass 961 (M+).

EXAMPLE 2

Preparation of a Linear MMA-BuA-MMA Triblock Copolymer in a Solvent Medium 320 g (i.e. 2.5 mol) of butyl acrylate and 6.8 g (i.e. 7.1 mmol) of polyalkoxyamine prepared in Example 1 are introduced at ambient temperature into a 1 l reactor equipped with a jacket. After degassing several times with nitrogen, the reaction medium is brought to 115° C. and this temperature is maintained for 5 h by thermal regulation. Samples are withdrawn throughout the reaction in order:

to determine the kinetics of the polymerization by gravimetry (measurement of solids contents);
  to monitor the change in the molecular masses as a function of the conversion.

When a conversion of 80% is achieved, the reaction medium is cooled to 60° C. and the residual butyl acrylate is removed by evaporation under vacuum.

391 g (i.e. 3.7 mol) of methyl methacrylate and 78 g of toluene are then added at 60° C. The reaction medium is subsequently heated at 95° C. for 2 h (conversion=50%). After returning to 60° C. and diluting with 78 g of toluene, the MMA-BuA-MMA copolymer is withdrawn from the reactor and the residual monomers and solvent are removed by evaporation under vacuum.

The MMA-BuA-MMA copolymer is analysed by GPC (Gel Permeation Chromatography), LAC (Liquid Adsorption Chromatography) and the solvent gradient HPLC technique, which makes it possible to separate the polymers according to their chemical composition and is independent of their molar mass under defined experimental conditions. The rheological properties of the polymers obtained are illustrated by a DMA (Dynamic Mechanical Analysis) study.

Characterization by GPC (Gel Permeation Chromatography)

| Example 2 | Mn | Mw | Mp | Pl |
|---|---|---|---|---|
| PBuA | 23 200 | 29 780 | 29 690 | 1.3 |
| PMMA-PBuA-PMMA | 61 110 | 124 500 | 98 910 | 2.0 |

The molar masses are expressed in PMMA equivalents.

Characterization by LAC (Liquid Adsorption Chromatography), see FIG. 1

The chromatogram presented in FIG. 1 represents the superposition of the chromatograms obtained by LAC for the PBuA polymer synthesized during the first stage, the final PMMA/PBuA/PMMA copolymer and a PMMA standard. The peak corresponding to the initial PBuA exhibits an elution volume of the order of 67 ml, whereas the peak of the final copolymer is markedly displaced towards the region richer in PMMA (Elution volume=110 ml). This very marked different in the elution volume between these two peaks clearly shows an internal change in the composition of the chains of the polymer and constitutes the evidence for reinitiation of the living PBuA chains and for attachment of the MMA units.

Figure 2:
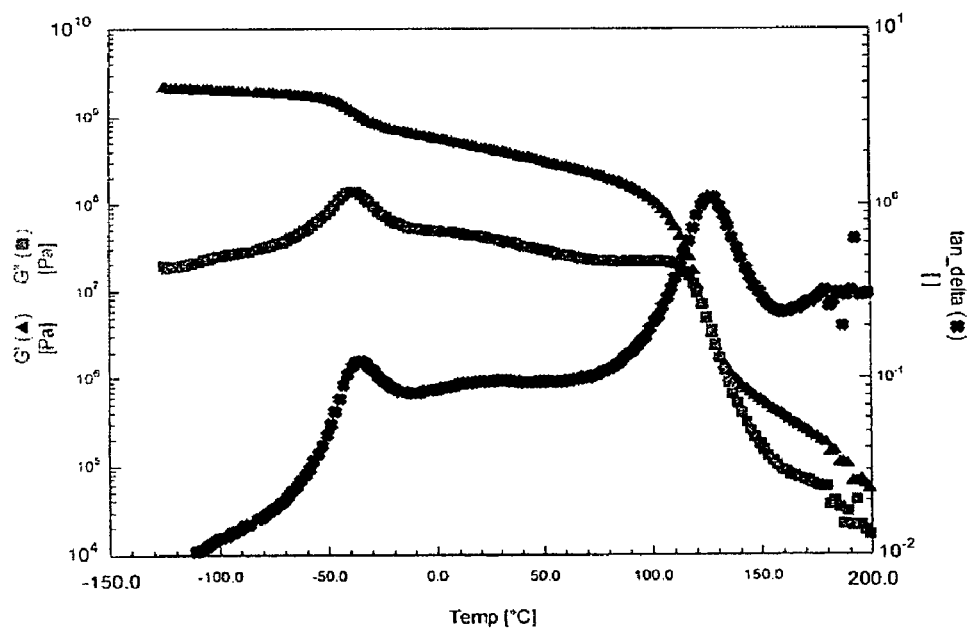
FIG. 2 is a characterization by Dynamic Mechanical Analysis of PMMA/PBuA/PMMA copolymer.

Characterization by DMA (Dynamic Mechanical Analysis), see FIG. 2

The DMA of the PMMA-PBuA-PMMA copolymer was carried out on a strain-controlled viscoelastometer (Ares). The geometry used is rectangular torsion for a temperature range of between −125° C. and 200° C. at a frequency of 1 Hz. The sample, in the form of a plaque, was moulded by composition at 170° C.

The curve obtained clearly shows a rubbery plateau between the glass transitions of the two types of blocks. The G' modulus reflects the average chemical composition of the polymer obtained.

| Reference | Tg (BuA) | Tg | Tg (PMMA) |
|---|---|---|---|
| PMMA-PBuA-PMMA | −34.9 | 29.3 | 127 |

EXAMPLE 3

Preparation of a Linear MMA-BuA-MMA Triblock Copolymer in a Dispersed Medium

The MMA-BuA-MMA triblock copolymer is prepared in three stages:

On the one hand, an organic solution is prepared by mixing:
- 148 g (i.e. 1.2 mol) of butyl acrylate,
- 2.9 g (i.e. 3.0 mmol) of polyalkoxyamine prepared in Example 1,
- 0.15 g of a polystyrene with a weight-average molecular mass (Mw) of 300 000,
- 1.33 g (i.e. 5.9 mmol) of hexadecane.

On the other hand, an aqueous solution is prepared by mixing:
- 595 g of water,
- 3.33 g (i.e. 4.0 mmol) of Dowfax 8390® emulsifying agent sold by Dow Chemical (mixture of mono- and of dihexadecyl disodium diphenyl oxide disulphonate),
- 0.64 g (i.e. 7.6 mmol) of $NaHCO_3$.

These two solutions are subsequently mixed for 10 min using a magnetic stirrer. The mixture is subsequently subjected to strong turbulence by a very powerful ultrasonic probe (of Branson 450 type, power 7) for 10 min, so as to obtain an emulsion, the size of the drops of which is of the order of 10 nm.

The emulsion is subsequently introduced into a 1 l reactor equipped with a jacket and is degassed with nitrogen for 10 min. The reaction medium is then brought to 120° C. and this temperature is maintained for 5 h by thermal regulation. Samples are withdrawn throughout the reaction in order:
- to determine the kinetics of the polymerization by gravimetry (measurement of solids contents),
- to monitor the change in the molecular masses as a function of the conversion.

When a conversion of 70% is achieved, the reaction medium is cooled to ambient temperature and a solution comprising 78 g (i.e. 0.7 mol) of methyl methacrylate, 269 g of water and 1.9 g (i.e. 2.3 mmol) of Dowfax 8390 emulsifying agent is added at this same temperature.

The reaction medium is subsequently heated at 100° C. for 6 h (conversion=70%) and is then cooled to ambient temperature. A solution comprising 0.2 g (i.e. 0.7 mmol) of potassium persulphate in 8 g of water is then added to remove the traces of residual monomers. After heating at 75° C. for 2 h and returning to ambient temperature, the latex is withdrawn from the reactor.

The latex is subsequently analysed by CHDF (Capillary Hydrodynamic Fractionation), GPC (Gel Permeation Chromatography), LAC (Liquid Adsorption Chromatography) and DMA (Dynamic Mechanical Analysis).

The invention claimed is:

1. Process for the preparation of polyalkoxyamines having functional groups:

$$-Z-\left[\begin{array}{c} C(CH_3)_3 \\ | \\ (CH_3)C-N-CH-P(O)(OEt)_2 \\ | \\ O \quad\quad R_1 \\ | \quad\quad | \\ CH-CH_2-C-R_1 \\ | \\ COOR_2 \end{array}\right]_m$$

in which m is an integer greater than or equal to 2 and less than or equal to n, which comprises reacting at least one monoalkoxyamine(s) of formula (I)

$$\begin{array}{cc} R_1 & C(CH_3)_3 \\ | & | \\ R_1-C-O-N-CH-C(CH_3)_3 \\ | & | \\ C(O)OR_2 & P(O)(OEt)_2 \end{array} \quad (I)$$

in which $R_1$ represents a linear or branched alkyl radical having a number of carbon atoms ranging from 1 to 3 and $R_2$ represents a hydrogen atom, a liner or branched alkyl radical having a number of carbon atoms ranging from 1 to 8, a phenyl radical, an alkali metal, selected from the group consisting of Li, Na or K, or an ammonium ion, selected from the group consisting of $NH_4^+$, $NBu_4^+$ or $NHBu_3^+$; with at least one polyunsaturated compound of formula (II):

$$Z-[CH=CH_2]_n \quad (II)$$

in which Z is an aryl group or $Z_1$-[X—C(O)]$_n$ where $Z_1$ represents a polyfunctional structure, X is an oxygen atom, a nitrogen atom carrying a carbonaceous group, a hydrogen atom, or a sulphur atom, and n is an integer greater than or equal to 2, at a reaction temperature f between about 0 and 90° C., the molar ratio of monoalkoxyamine(s) of formula (I) to polyunsaturated compound(s) of formula (II) being between 1.5 and 1.5 n.

2. Process according to claim 1, characterized in that said reacting occurs in the presence of a solvent selected from the group consisting of alcohol, aromatic solvents, chlorinated solvents, ethers, polar aprotic solvents, or mixtures thereof.

3. Process according to claim 1, characterized in that the reaction temperature is between about 25 and 80° C.

4. Process according to claims 1, characterized in that compound is chosen from divinylbenzene, trivinylbenzene, ethylene glycol diacrylate, 1,3-butanediol diacrylate, 1,4-butanediol diacrylate, 1,6-hexanediol diacrylate, neopentyl glycol diacrylate, cyclohexanedimethanol diacrylate, diethylene glycol diacrylate, triethylene glycol diacrylate, tetraethylene glycol diacrylate, dipropylene glycol diacrylate, tripropylene glycol diacrylate, polyethylene glycol diacrylates, hexanediol alkoxylate diacrylates, bisphenol A diacrylate, bisphenol A ethoxylate diacrylates, trimethylolpropane triacrylate, pentaerythritol triacrylate, tris(2-hydroxyethyl) isocyanurate triacrylate, trimethylolpropane ethoxylate triacrylates, glyceryl propoxylate triacrylate, trimethylolpropane propoxylate triacrylates, pentaerythritol tetraacrylate, ditrimethylolpropane tetraacrylate, pentaerythritol ethoxylate tetraacrylate, dipentaerythritol pentaacrylate, caprolactones modified dipentaerythritol hexaacrylates or dipentaerythritol pentaacrylate.

5. Process for the preparation of polyfunctional living (co)polymers by polymerization by the radical route of one or more vinyl monomers in the presence of polyalkoxyamines prepared beforehand according to the process of claim 1.

6. Process for the preparation of polyfunctional living (co)polymers according to claim 5, characterized in that the polyalkoxyamines are prepared prior to the (co)polymerization.

7. Process for the preparation of polyfunctional living (co)polymers according to claim 5, characterized in that the polyalkoxyamines are prepared simultaneously with the (co)polymerization.

8. Process according to claim 5, characterized in that it is carried out in bulk, in solution, in emulsion, in miniemulsion or in suspension at a polymerization temperature greater than about 90° C.

9. Process according to claim 5, characterized in that the vinyl monomers are chosen from styrene, substituted styrenes, dienes, acrylic monomers, methacrylic monomers.

10. Process according to claim 5 further comprising at least one polymerization initiator selected from the group consisting of organic peroxides, inorganic peroxides, azo compounds or other alkoxyamines.

11. Process of claim 1 characterized in that said reacting occurs under a nitrogen atmosphere.

12. Process of claim 1, characterized in that $R_1$ is $CH_3$ and $R_2$ is H.

13. Process of claim 1, characterized in that the molar ratio of monoalkoxyamine(s) of formula (I) to polyunsaturated compound(s) of formula (II) is between n and 1.25 n.

14. Process of claim 2, further comprising evaporation of said solvents after said reacting.

15. Process of claim 9 characterized in that said diene is selected from the group consisting of butadiene or isoprene.

16. Process of claim 9 characterized in that said acrylic monomers are selected from the group consisting of acrylic acid, alkyl acrylates, aryl acrylates, or functional acrylates.

17. Process of claim 16 characterized in that said acrylic monomers are halogenated.

18. Process of claim 16 characterized in that said acrylic monomers are a carrier of siloxane functional groups.

19. Process of claim 9 characterized in that said methacrylic monomers are selected from the group consisting of methyl methacrylate, alkyl methacrylate, functional methacrylate or mixtures thereof.

20. Process of claim 19 characterized in that said methacrylic monomers are halogenated.

21. Process of claim 19 characterized in that said methacrylic monomers are a carrier of siloxane functional groups.

22. Process of claim 19 characterized in that said methacrylic monomers are selected form the group N,N-dimethylacrylamide, 4-acryloylmorpholine, methacrylamide; substituted methacrylamides, vinylpyridine, vinylpyrrolidinone, vinyl chloride, vinylidene difluoride or mixtures thereof.

23. Process of claim 8 characterized in that said solution is aqueous.

24. Process of claim 8 characterized in that said solution is organic.

* * * * *